US012778989B2

(12) United States Patent
Hua et al.

(10) Patent No.: US 12,778,989 B2
(45) Date of Patent: Nov. 3, 2026

(54) **EFFICIENT TRACELESS GENE EDITING SYSTEM FOR *SALMONELLA* AND USE THEREOF**

(71) Applicant: JIANGSU TARGET BIOMEDICAL RESEARCH INSTITUTE CO., LTD., Changzhou (CN)

(72) Inventors: Zichun Hua, Changzhou (CN); Jiahuang Li, Changzhou (CN); Chao Han, Changzhou (CN); Menghui Wang, Changzhou (CN); Junjie Zhou, Changzhou (CN); Jing Li, Changzhou (CN)

(73) Assignee: Jiangsu Target Biomedical Research Institute Co., Ltd., Changzhou (CN)

( * ) Notice: Subject to any disclaimer, the term of this patent is extended or adjusted under 35 U.S.C. 154(b) by 866 days.

(21) Appl. No.: 18/548,158

(22) PCT Filed: Oct. 29, 2020

(86) PCT No.: PCT/CN2020/124685
§ 371 (c)(1),
(2) Date: Aug. 28, 2023

(87) PCT Pub. No.: WO2021/184763
PCT Pub. Date: Sep. 23, 2021

(65) Prior Publication Data

US 2024/0197792 A1 Jun. 20, 2024

(30) Foreign Application Priority Data

Mar. 16, 2020 (CN) ........................ 202010182038.0

(51) Int. Cl.
*A61K 35/74* (2015.01)
*A61P 35/00* (2006.01)
(Continued)

(52) U.S. Cl.
CPC .............. *A61K 35/74* (2013.01); *A61P 35/00* (2018.01); *C12N 9/1241* (2013.01); *C12N 9/22* (2013.01);
(Continued)

(58) Field of Classification Search
CPC ....... A61K 35/74; A61K 35/741; A61P 35/00; C12N 9/1241; C12N 9/22; C12N 15/11;
(Continued)

(56) References Cited

FOREIGN PATENT DOCUMENTS

| | | |
|---|---|---|
| CN | 109825522 A | 5/2019 |
| CN | 111454927 A | 7/2020 |
| CN | 112980891 A | 6/2021 |

OTHER PUBLICATIONS

Jiang, Y. et al., "Multigene Editing in the *Escherichia coli* Genome via CRISPR-Cas9 System", Applied and Environmental Microbiology, Apr. 30, 2015, pp. 2506-2514, vol. 81, No. 7, ROI: 114.212.247.93, aem..asm.org.

(Continued)

*Primary Examiner* — Tracy Vivlemore
*Assistant Examiner* — Thomas R. Amick
(74) *Attorney, Agent, or Firm* — Hudak, Shunk & Farine Co. LPA

(57) ABSTRACT

An efficient and scarless gene editing system for *Salmonella* and the use thereof are provided. λRed recombinase is used to promote a double crossover of a DNA template with a genomic target site, the CRISPR/Cas9 system is used for screening, and one-step homologous recombination is used to rapidly construct a targeting plasmid, which can realize insertion, substitution or knock-out of genes. Genomic DNA is completely substituted according to a design of homologous template, and without other fragment residues. Genome editing can be completed efficiently within 3-4 days, thereby reducing the experimental workload and shortening the experimental cycle.

11 Claims, 7 Drawing Sheets

Specification includes a Sequence Listing.

(51) Int. Cl.
*C12N 9/12* (2006.01)
*C12N 9/22* (2006.01)
*C12N 15/11* (2006.01)
*C12N 15/74* (2006.01)
*C12N 15/90* (2006.01)

(52) U.S. Cl.
CPC .............. *C12N 15/11* (2013.01); *C12N 15/74* (2013.01); *C12N 15/902* (2013.01); *C12Y 207/07047* (2013.01); *C12N 2310/20* (2017.05); *C12N 2800/101* (2013.01); *C12N 2800/40* (2013.01); *C12N 2800/80* (2013.01)

(58) Field of Classification Search
CPC .................. C12N 15/74; C12N 15/902; C12N 2310/20; C12N 2800/101; C12N 2800/40; C12N 2800/80; C12N 15/102; C12N 15/113; C12Y 207/07047; Y02A 50/30
See application file for complete search history.

(56) References Cited

OTHER PUBLICATIONS

Silva-Valenzuela, C.A. et al., "Solid Tumors Provide Niche-specific Conditions That Led to Preferential growth of *Salmonella*", Oncotarget, Apr. 28, 2016, pp. 35169-35180, vol. 7, No. 23, www.impactjournals.com/oncotarget.

Tarverdizadeh et al., Targeted gene inactivation in *Salmonella* Tphi by CRISPR/Cas9-assisted homologous recombination, World Journal of Microbiology and Biotechnology, Dec. 27, 2022, pp. 1-9, Springer.

Li et al., A modified pCas/pTargetF system for CRISPR-Cas9-assisted genome editing in *Escherichia coli*, Acta Biochim Biophys Sin, Mar. 25, 2021, pp. 620-627, Oxford University Press on behalf of the Center for Excellence in Molecular Cell Science.

Li et al., Improving the Editing Efficiency of CRISPR-Cas9 by Reducing the Generation of Escapers Based on the Surviving Mechanism, ACS SyntheticBiology, Mar. 3, 2023, vol. 12, pp. 672-680, American Cemical Society.

Vento et al., Barriers to genome editing with CRISPR in bacteria, Journal of Industrial Microbiology & Biotechnology, Jun. 5, 2019, 15 pages, Springer.

Leenay et al., Genome Editing with CRISPR-Cas9 in Lactobacillus plantarum Revealed That Editing Outcomes Can Vary Across Strains and Between Methods, Biotechnology Journal, Aug. 29, 2018, pp. 1-11, Wiley-VCH Verlag Gmbh & Co. KGaA, Weinheim.

Randall et al., Antibiotic resistance genes, integrons and multiple antibiotic resistance in thirty-five serotypes of *Salmonella enterica* isolated from humans and animals in the UK, Journal of Antimicrobial Chemotherapy, Jan. 16, 2024, vol. 53, No. 2, pp. 208-216, Crown.

Guerra, et al., Antimicrobial Resistance and Spread of Class 1 Integrons among *Salmonella* Serotypes, Antimicrobial Agents and Chemotherapy, Aug. 1, 2000, pp. 2166-2169, American Society for Microbiology.

1. msbB::RFP; 2. pCas-VNP

1. PBS; 2. eutC::RFP; 3. msbB::RFP

1. PBS; 2. eutC::RFP; 3. msbB::RFP

EFFICIENT TRACELESS GENE EDITING SYSTEM FOR *SALMONELLA* AND USE THEREOF

INCORPORATED BY REFERENCE

The instant application contains a Sequence Listing which has been submitted electronically in ASCII format and is hereby incorporated by reference in its entirety. Said ASCII copy is named SequenceListingPCTCN2020124172.txt and is 13 kilobytes in size.

FIELD OF THE INVENTION

The present invention relates to the field of genetic engineering, and specifically, to an efficient and traceless gene editing system for *Salmonella* and its use.

BACKGROUND OF THE INVENTION

*Salmonella* is a common zoonotic pathogen and the most common pathogenic bacteria of bacterial food infections in countries, which can lead to a variety of syndromes such as gastroenteritis, typhoid fever, septicemia and extraintestinal focal infections. Modification of the *Salmonella* genome through genome editing technology to obtain strains with different genetic backgrounds can help study the mechanisms of *Salmonella* growth, reproduction and its pathogenic process, thereby laying a foundation for prevention and treatment. Attenuated *Salmonella* may also be used in tumor treatment, for example, it has been found that attenuated *Salmonella* strain VNP20009 has a certain therapeutic effect on a variety of tumors in animal models. Genetic modification of the *Salmonella* genome is an important means to further enhance its therapeutic effect, which can be achieved by modifying the genes related to invasion, motility or metabolism of the *Salmonella* genome, or by integrating therapeutic genes into the bacterial chromosome and with the stable expression thereof, to improve the therapeutic effect, or by integrating a reporter gene into the chromosome and with the stable expression thereof, to achieve in vivo tracing.

The λ phage-based Red homologous recombination system is a commonly used method for modifying bacterial genomes and has been used in *Escherichia coli* [Datsenko, K. A. 2000] and *Salmonella* [Husseiny M I et al, 2005; Solano C et al, 2010]. The genome after knock-out by the Red homologous recombination method will have a resistance gene screening marker, or a residual FRT (recombinase FLP recognition site) sequence trace of about 80 bp after removal of the marker [Datsenko, K. A. 2000]. The residual scarsequence may limit the use of the system for further modification of other genes. Recently, some traceless gene editing methods have been developed, such as the traceless editing systems based on I-SceI and λRed [Kim J et al. 2014; Blank K et al. 2011], however, these methods still have the drawbacks of cumbersome experimental process, long cycle time, and difficulty in large fragment insertion.

The adaptive immune systemCRISPR-Cas9 (clustered regularly interspaced short palindromic repeats/CRISPR-associated proteins), derived from *Streptomyces*, is an efficient gene editing tool that has emerged in recent years and has been applied to many eukaryotic cells and prokaryotic cells including *E. coli, Streptomyces, Clostridium*, and *Lactobacillus* [Jiang Y et al. 2015]. The CRISPR/Cas9 system comprises two components: sgRNA and nuclease Cas9.

Targeting the target site of the genome is carried out by sgRNA through a specific 20-base sequence, and sgRNA mediates Cas9 cleavage of the site's DNA double strand, which can increase the proportion of homologous recombination or serve for screening. However, can this gene editing tool derived from *Streptomyces* be applied to *Salmonella*? If yes, what modifications should be made to facilitate genome editing in *Salmonella*? These problems have not been explored and studied.

Currently, there is a lack of a fast and efficient traceless gene editing system for *Salmonella* and its use.

SUMMARY OF THE INVENTION

The objective of the present invention is to provide an efficient traceless gene editing system for *Salmonella* and use thereof.

In order to solve the technical problem identified above, the present invention provides the following technical solution: An efficient and traceless gene editing system for *Salmonella*, comprising: a Cas9 protein, a sgRNA, a λRed recombinase and a homologous recombinant DNA fragment, and vectors and gene sequences for carrying or expressing the same.

Further, the efficient and traceless gene editing system for *Salmonella* consists of a dual plasmid CRISPR/Cas9 system comprising a helper plasmid A expressing a relevant functional protein and a targeting plasmid B expressing a target site sgRNA.

Further, the helper plasmid A comprises nucleic acid sequences of components: a Cas9 protein, a λRed recombinase, a temperature-sensitive replicon, an sgRNA expression frame of the targeting plasmid B replicon, and a helper plasmid A screening marker gene, and wherein the recombinase and sgRNA are inducibly expressed.

Further, the targeting plasmid B comprises nucleic acid sequences of components: a replicon, a targeting plasmid screening marker gene, an sgRNA expression frame for a target site, and a DNA fragment for homologous recombination, and wherein the replicons of the helper plasmid A and the targeting plasmid B are capable of being replicated in *Escherichia coli* and *Salmonella*, the replicon and the screening marker gene of the plasmid B are different from the replicon and the screening marker gene of the plasmid A, and the replicon of the targeting plasmid B is compatible with the replicon of the helper plasmid A.

Further, the sgRNA expression frame has a promoter-(N)X-sgRNA backbone-terminator structure, and the target site DNA has a 5'-(N)X-NGG-3' structure, and wherein (N)X denotes X Ns, N is any of the bases A, T, C or T, and X is an integer greater than 15 and less than 25.

Further, the X of the target site DNA is 20, and the homologous recombinant DNA fragment is upstream homology arm-insert fragment-downstream homology arm when used for knock-in or substitution, and upstream homology arm-downstream homology arm when used for knock-out; the DNA fragment is constructed in the targeting plasmid B or in a PCR product; and the gene editing system is capable of gene editing on multiple target sites simultaneously.

Further, the targeting plasmid B comprises editing modules for multiple target sites with a structure of plasmid backbone (resistance gene-replicon)-editing module 1 (target site 1 sgRNA expression frame-upstream homology arm 1-knock-in (or substitution) fragment-downstream homology arm 1)-editing module 2 (target site 2 sgRNA expression frame-upstream homology arm 2-knock-in (or substitution)

fragment-downstream homology arm 2)-editing module n; however, the success rate of editing gradually decreases with the increase of target sites, and due to the time cost of plasmid construction, generally the number target sites is not greater than 3.

A method of constructing the targeting plasmid B of the present invention, comprises the following steps:

1) for knock-in (or substitution): amplifying the targeting plasmid B backbone, the target site sgRNA expression frame, the upstream/downstream homology arms, and the knock-in (or substitution) fragment, respectively, and ligating all DNA fragments using one-step homologous recombination;
2) for knock-out: amplifying the targeting plasmid B backbone, the target site sgRNA expression frame, and the upstream/downstream homology arms, respectively, and ligating all DNA fragments using one-step homologous recombination;
3) for targeting plasmid B contain in no homology arms, amplifying the upstream/downstream homology arms respectively, and ligating them as a linear DNA template.

Use of the efficient traceless gene editing system for *Salmonella* in genome editing, comprises the following steps:

1) introducing the helper plasmid A into *Salmonella* and inducing a λRed recombinase expression to prepare competent cells;
2) introducing the targeting plasmid B and a linear DNA template to the competent cells of step 1), or introducing a targeting plasmid B comprising the template DNA;
3) resuscitating the cells from step 2) and coating on a plate comprising two resistances corresponding respectively to the plasmid A and the plasmid B, and screening for positive clones with double crossover;
4) after performing PCR or sequencing verification of the positive clones, inducing sgRNA expression of the targeting plasmid B replicon and eliminating the plasmid B;
5) after verifying the elimination of the plasmid B, increasing the bacterial culture temperature and eliminating the plasmid A to obtain a successfully modified *Salmonella* clone.

Further, at the end of step 4), the plasmid A is retained, and step 2) is repeated to introduce the targeting plasmid B and a template DNA for targeting other loci.

Use of the efficient and traceless gene editing system for *Salmonella* in *Salmonella* genome editing.

Use of the efficient and traceless gene editing system for *Salmonella* in preparation of a *Salmonella* antitumor drug.

Use of the efficient and traceless gene editing system for *Salmonella* in preparation of an eutC gene-deficient *Salmonella* by genome editing.

Use of the genome edited eutC gene-deficient *Salmonella* in preparation of *Salmonella* antitumor drugs.

In one embodiment of the present invention, the plasmid A is pCas [6] and comprises: a constitutively expressed Cas9 protein, a λRed recombinase (three proteins, i.e. Exo, Beta and Gam), a promoter ParaB of λRed which is induced to be expressed by L-arabinose, a temperature-sensitive replicon repA101, a sgRNA expression frame of the targeting plasmid B replicon, a promoter Ptrc of sgRNA which is regulated by a lactose manipulator; a kanamycin resistance gene, and a lactose deterrent protein lacl.

In one embodiment of the present invention, the plasmid B is a pTAT plasmid, which is formed by ligating fragment 1 plasmid backbone (comprising: a pMB1 replicon, and an ampicillin resistance gene), fragment 2 target site sgRNA expression frame, and fragment 3 template DNA (homology arm upstream of the target site, exogenous insertion DNA, homology arm downstream of the target site). The order of ligation can be varied in practice).

Beneficial effects: With the CRISPR/Cas9 system, the present invention uses the target site (N) X-NGG sequence of the genome as the target site for reverse screening of wild-type *Salmonella* to establish an efficient, stable and traceless gene editing method for *Salmonella*. The method uses a constitutive promoter to continuously express Cas9 protein and the target site sgRNA, and continuously cuts the DNA double strand at the (N) X-NGG sequence of the wild-type bacteria, and the bacteria will not survive if they cannot or are too slow to repair the DNA damage. Only positive clones that the target site DNA is double-cross-overed with the template DNA, either spontaneously or with the aid of the λRed recombinase, does not have the (N) X-NGG sequence, and can survive. The inducibly expressed sgRNA is also used to cleave the replicon DNA of plasmid B. This allows for rapid elimination of plasmid B and improves the efficiency of the operation.

BRIEF DESCRIPTION OF THE DRAWINGS

The solution of the present invention will be better understood with Reference to the accompanying drawings, wherein.

DETAILED DESCRIPTION OF THE INVENTION

Figure 1:
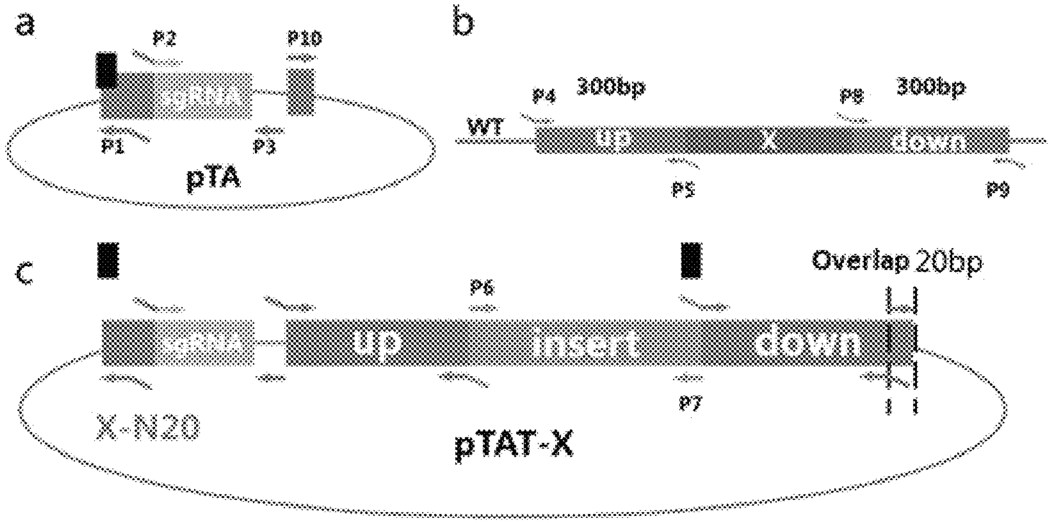
FIG. 1 shows a schematic diagram of the design and construction of the targeting plasmid B pTAT-X-insert of the present invention; P1 to P10 are primers, up: upstream homology arm of the target site, down: downstream homology arm of the target site, X: target site sequence, insert: insert fragment; a is a schematic diagram of the design of the pTA plasmid and its primers; b is a schematic diagram of the design of the wild-type *Salmonella* genome target site and its primers; c is a schematic diagram of the design of the pTAT-X plasmid and its primers.

The present invention will be described in further detail below with reference to the accompanying drawings.

The accompanying drawings and Examples of the present invention are intended to illustrate specific embodiments of the present invention in greater detail so that the solutions of the present invention and the advantages thereof can be better understood, but not intended to limit the present invention.

The present invention will be further described below by specific Examples. The methods involved in the Examples are conventional technical means known to one skilled in the art, unless specified otherwise. The experimental methods involved in the Examples have been performed for a long period of time, and more than 6 effective numerical ranges have been tried for concentration, time and primer sequence. The Examples list only one of the parameters, which is not the only optional parameter. The reagents, materials, etc., involved in the Examples are commercially available, unless specified otherwise.

An efficient and traceless gene editing system for *Salmonella*, comprising: a Cas9 protein, a sgRNA, a λRed recombinase and a homologous recombinant DNA fragment, and vectors and gene sequences for carrying or expressing the same.

Further, the efficient and traceless gene editing system for *Salmonella* consists of a dual plasmid CRISPR/Cas9 system comprising a helper plasmid A expressing a relevant functional protein and a targeting plasmid B expressing a target site sgRNA.

Further, the helper plasmid A comprises nucleic acid sequences of components: a Cas9 protein, a λRed recombinase, a temperature-sensitive replicon, an sgRNA expression frame of the targeting plasmid B replicon, and a helper plasmid A screening marker gene, and wherein the recombinase and sgRNA are inducibly expressed.

Further, the targeting plasmid B comprises nucleic acid sequences of components: a replicon, a targeting plasmid screening marker gene, an sgRNA expression frame for a target site, and a DNA fragment for homologous recombination, and wherein the replicons of the helper plasmid A and the targeting plasmid B are capable of being replicated in *Escherichia coli* and *Salmonella*, the replicon and the screening marker gene of the plasmid B are different from the replicon and the screening marker gene of the plasmid A, and the replicon of the targeting plasmid B is compatible with the replicon of the helper plasmid A.

Further, the sgRNA expression frame has a promoter-(N) X-sgRNA backbone-terminator structure, and the target site DNA has a 5'-(N)X-NGG-3' structure, and wherein (N)X denotes X Ns, N is any of the bases A, T, C or T, and X is an integer greater than 15 and less than 25.

Further, the X of the target site DNA is 20, and the homologous recombinant DNA fragment is upstream homology arm-insert fragment-downstream homology arm when used for knock-in or substitution, and upstream homology arm-downstream homology arm when used for knock-out; the DNA fragment is constructed in the targeting plasmid B or in a PCR product; and the gene editing system is capable of gene editing on multiple target sites simultaneously.

Further, the targeting plasmid B comprises editing modules for multiple target sites with a structure of plasmid backbone (resistance gene-replicon)-editing module 1 (target site 1 sgRNA expression frame-upstream homology arm 1-knock-in (or substitution) fragment-downstream homology arm 1)-editing module 2 (target site 2 sgRNA expression frame-upstream homology arm 2-knock-in (or substitution) fragment-downstream homology arm 2)-editing module n; however, the success rate of editing gradually decreases with the increase of target sites, and due to the time cost of plasmid construction, generally the number target sites is not greater than 3.

A method of constructing the targeting plasmid B of the present invention, comprises the following steps:

1) for knock-in (or substitution): amplifying the targeting plasmid B backbone, the target site sgRNA expression frame, the upstream/downstream homology arms, and the knock-in (or substitution) fragment, respectively, and ligating all DNA fragments using one-step homologous recombination;
2) for knock-out: amplifying the targeting plasmid B backbone, the target site sgRNA expression frame, and the upstream/downstream homology arms, respectively, and ligating all DNA fragments using one-step homologous recombination;
3) for targeting plasmid B contain in no homology arms, amplifying the upstream/downstream homology arms respectively, and ligating them as a linear DNA template.

Use of the efficient traceless gene editing system for *Salmonella* in genome editing, comprises the following steps:

1) introducing the helper plasmid A into *Salmonella* and inducing a λRed recombinase expression to prepare competent cells;
2) introducing the targeting plasmid B and a linear DNA template to the competent cells of step 1), or introducing a targeting plasmid B comprising the template DNA;
3) resuscitating the cells from step 2) and coating on a plate comprising two resistances corresponding respectively to the plasmid A and the plasmid B, and screening for positive clones with double crossover;
4) after performing PCR or sequencing verification of the positive clones, inducing sgRNA expression of the targeting plasmid B replicon and eliminating the plasmid B;
5) after verifying the elimination of the plasmid B, increasing the bacterial culture temperature and eliminating the plasmid A to obtain a successfully modified *Salmonella* clone.

At the end of step 4), the plasmid A is retained, and step 2) is repeated to introduce the targeting plasmid B and a template DNA for targeting other loci.

Use of the efficient and traceless gene editing system for *Salmonella* in *Salmonella* genome editing.

Use of the efficient and traceless gene editing system for *Salmonella* in preparation of a *Salmonella* antitumor drug.

Use of the efficient and traceless gene editing system for *Salmonella* in preparation of an eutC gene-deficient *Salmonella* by genome editing.

Use of the genome edited eutC gene-deficient *Salmonella* in preparation of *Salmonella* antitumor drugs.

In one embodiment of the present invention, the plasmid A is pCas [6] and comprises: a constitutively expressed Cas9 protein, a λRed recombinase (three proteins, i.e. Exo, Beta and Gam), a promoter ParaB of λRed which is induced to be expressed by L-arabinose, a temperature-sensitive replicon repA101, a sgRNA expression frame of the targeting plasmid B replicon, a promoter Ptrc of sgRNA which is regulated by a lactose manipulator; a kanamycin resistance gene, and a lactose deterrent protein lacl.

In one embodiment of the present invention, the plasmid B is a pTAT plasmid, which is formed by ligating fragment 1 plasmid backbone (comprising: a pMB1 replicon, and an ampicillin resistance gene), fragment 2 target site sgRNA expression frame, and fragment 3 template DNA (homology arm upstream of the target site, exogenous insertion DNA, homology arm downstream of the target site). The order of ligation can be varied in practice).

Example 1

Materials and Methods

1. Strains and Culture Method

The strains and plasmids used in this Example are listed in Table 1. Among them, *E. coli* DH5a was used as the clone strain, and *Salmonella* VNP20009 was the strain to be modified. All strains were cultured in LB medium at 37° C., except for the strain containing the pCas plasmid, which was cultured at 30° C., unless specified otherwise. The strains were incubated in a stationary incubator or in a shaker with shaking at 220 rpm. Bacterial growth was measured using an Eppendorf spectrophotometer to determine the light absorption value at 600 nm (OD600).

LB medium formulation: tryptone 10 g/L, yeast extract 5 g/L, sodium chloride 10 g/L, solid medium with agar 15 g/L. Antibiotics were added to the medium as needed: kanamycin (Kan+) at a working concentration of 50 mg/L, ampicillin (Amp+) at a working concentration of 100 mg/L. L-arabinose and IPTG were used as inducers, and added to the medium at the concentrations provided in the following steps. The strains and plasmids used in the present invention are shown in Table 1.

TABLE 1

| Strains or Plasmids | Properties | Source |
|---|---|---|
| Strains | | |
| DH5a | deoR endA1 gyrA96 hsdR17 (rk-mk+) recA1 relA1 supE44 thi-1 Δ(lacZYA-argF)U169 Φ80lacZ ΔM15 F-λ- | Vazyme |
| VNP20009 | msbB purI xyl EGTAr | ATCC |
| Plasmids | | |
| pET-22b(+) | AmpR | Novagen |
| pCas | repA101(Ts) kan Pcas-cas9 ParaB-Red lacIq Ptrc-sgRNA-pMB1 | [6] |
| pTargetF-cadA | pMB1 aadA cadA-sgRNA | [6] |
| pTargetT-msbB-RFP | pMB1 aadA msbB-sgRNA ΔmsbB::RFP | The present invention |
| pTAT-msbB-RFP | pMB1 amp msbB-sgRNA ΔmsbB::RFP | The present invention |
| pTAT-eutC2-RFP | pMB1 amp eutC-sgRNA ΔeutC::RFP | The present invention |

2. Reagent Materials

Plasmid extraction kit and agarose gel purification kit for PCR product purification were commercially available from TIANGEN. High-fidelity PCR enzyme pre-mix 2× Phanta Max Master Mix used for the fragments for plasmid construction, rapid PCR enzyme pre-mix 2× Rapid Taq Master Mix used for PCR identification, and homologous recombination one step cloning kit, i.e. ClonExpress MultiS One Step Cloning Kit, used for ligation of DNA fragments were all commercially available from Nanjing Vozyme Biotech Co., Ltd.

All reagents were commercially available.

3. PCR Conditions

Unless specified otherwise, the reaction system for obtaining a PCR product is shown in Table 2:

TABLE 2

| | |
|---|---|
| 2 × Phanta Max Master Mix | 25 μL |
| Primer F | 2 μL |
| Primer R | 2 μL |
| Template | 1 μL |
| $ddH_2O$ | 20 μL |
| Total | 50 μL |

PCR reaction conditions were 94° C. for 5 min, 30 cycles (94° C. for 15 s, 56-58° C. for 15 s, 72° C. for 5 min), 72° C. for 7 min, 16° C. Reaction time at 72° C. was calculated based on 30 s/kb.

The reaction system for PCR identification to check the length of DNA fragments is shown in Table 3.

TABLE 3

| | |
|---|---|
| 2 × Rapid Taq Master Mix | 10 μL |
| Primer F | 1 μL |
| Primer R | 1 μL |
| Template | 1 μL |
| $ddH_2O$ | 7 μL |
| Total | 20 μL |

PCR reaction conditions were 94° C. for 5 min, 30 cycles (94° C. for 15 s, 56-58° ° C. for 15 s, 72° C. for 5 min), 72° C. for 7 min, 16° C. Reaction time at 72° C. was calculated based on 15 s/kb.

4. DNA Ligation and Transformation.

DNA fragment homologous recombination and transformation conditions. The reaction system was prepared on ice as shown in Table 4 below.

TABLE 4

| | |
|---|---|
| Linearized vector | X μL |
| n insertion fragments | $Y_1 - Y_n$ μL |
| 5 × CE MultiS Buffer | 4 μL |
| Exnase MultiS | 2 μL |
| $ddH_2O$ | To 20 μL |

The volume of each DNA fragment was calculated according to the ClonExpress MultiS One Step Cloning Kit Instruction Manual, the optimal amount for each fragment was [0.02×number of fragment base pairs] ng (0.03 pmol), the amount of linearized cloning vector should be between 50 ng and 200 ng, and the amount of each inserted fragment should be greater than 10 ng.

Recombination product was taken as 10 μL and added to 100 μLDH5a competent cells and placed on ice for 30 min. Heat-excited at 42° C. for 60 s and then immediately placed on ice to cool for 3 min. 900 μL of antibiotic-free LB medium was added and shaken at 37° C. for 1 h. Centrifuged at 5000 g for 5 min, and 900 μL supernatant was discarded.

The bacteria were re-suspended in the remaining medium, and coated on a culture plate with correct resistance and subjected to an inverted incubation overnight at 37° C.

5. DNA Sequencing

The plasmids or bacteria solutions were sent to Nanjing Kingsley Biotechnology Co. Ltd (Kingsley) for DNA sequencing.

6. *Salmonella* Competence Preparation

The day before the experiment, *Salmonella* VNP20009 strain was inoculated in 3 ml LB medium and incubated overnight at 37° C. with shaking. 2) The next day, it was transferred to fresh LB medium and incubated with shaking, and when the OD600 was about 0.8, the bacteria were collected by centrifugation at 5000 g for 4 min. 3) The bacteria were washed with 10% glycerol for three times, and the number of bacteria was adjusted to $1\times10^9$ CFU per tube, and finally, the bacteria were re-suspended in 80 μL of 10% glycerol.

7. *Salmonella* Electrotransformation

X μg plasmid was added to *Salmonella* VNP20009 competence, mixed fully, and then added to 2 mm Bio-Rad electroporation cup. 2) Gene Pulser Xcell™ electroporator was used for electroporation, with electroporation parameters set to 2400V, 25 μF, 400Ω. 3) After electrotransformation, resuscitated for 1 hr. in antibiotic-free LB at a suitable temperature, and then coated on aLB plate with corresponding resistance and subjected to an inverted incubation overnight at a suitable temperature.

Example 2 Design and Construction of Gene Editing System msbB modification site selection and sgRNA design. The full sequence data of the genome of *Salmonella typhimurium* strain VNP20009 was obtained from the NCBI database under the accession number CP007804.2. Part of the msbB gene between the pykA and yebA genes of *Salmonella* strain VNP20009 was missing. Firstly, we chose to insert a fragment between these two gene loci to substitute the 529 bp genomic sequence (CP007804.2, 1,886,524-1,887,052), which was not expected to change the characteristics of the strain. A sequence with a 5'-$(N)_X$-NGG-3' structure was selected from the substituted sequence, with $(N)_X$ denoting X N's, N being any of the bases A, T, C, or T, and X being a natural number greater than 15 and less than 25. In this Example, one sequence was selected: atgtcgacgccccagccatg, i.e., msbB-N20, and based on the selected N20 sequence, the primer pTargetF-msbB-F (sequence: atgtcgacgcccccagccatggttttagagagctagaaatagc) was designed to construct a targeting plasmid, thereby expressing sgRNA that can mediate Cas9 protein cleavage of the corresponding target site of msbB gene.

TagRFP-ORF design. Terminator B0014-promoter J23100-ribosome binding site B0034-TagRFP protein-terminator B0015, totaling 1073 bp, was synthesized by Kingsley. The specific sequence is shown as sequence 1 in the Sequence Listing.

Plasmid BpTAT-X-insert design and construction (FIG. 1). Primers were designed (see Table 5), and the vector, target gene sgRNA, upstream homology arm of the target gene, insert fragment, and downstream homology arm of the target gene were amplified by PCR, respectively. The above DNA fragments have 15-20 bp homologous sequences between two of them, which can be used to link multiple fragments by one-step homologous recombination and thus shorten the experimental cycle.

The target gene sgRNA guides the Cas9 cleavage site target DNA sequence, which has a 5'-$(N)_X$-NGG-3' structure. The method is designed without INSERT fragment. By directly connecting the upstream and downstream homology arms of the target gene, gene knock-out can be performed.

When the method is used to perform point mutation, genomic site mutation can be performed by designing primer PCR to obtain a homologous template carrying the mutation site. The primers used in this Example are shown in Table 5.

TABLE 5

| Primer | Sequence (5'-3') | Use |
|---|---|---|
| PT V-F | atgccgctcgccagtcga | pTargetF vector |
| pT V-R | ctcgagtagggataacagggtaataga | |
| pT amp-F | ccctgttatccctactcgagttaccaatgcttaatcagtgaggc | AmpR |
| pT amp-R | aatcgactggcgagcggcatcgcggaacccctatttgtt | |
| pTargetF-msbB-R | catggctggggcgtcgacatactagtattatacctaggac | pTA vector |
| pTA-vector-R | gcttagatctattaccctgttatcc | |
| pTargetF-msbB-F | atgtcgacgccccagccatggttttagagctagaaatagc | msbB-sgRNA |
| pTA-vector-F | ttctgcaggtcgactctagagag | |
| pTA-RFP on-F | tctagagtcgacctgcagaacatcaccgcaacgcaaat | Upstream homology arm of |
| RFP-msbB-up-R | tttgggcaaaaaatggcggcg | msbB |
| rfp-msbb-mid-f | gccgccatttttgcccaaatcccttataagaattctcacactgg | RFP-ORF |
| RFP-msbB-Mid-R | ggctttttgggatcccagtgatggttaaccc | |
| rfp-msbb-lower-f | actgggatcccaaaaaagccggcacacatc | downstream homology arm of |
| pTA-RFP down-R | acagggtaatagatctaagcttactacgccattcgcgc | msbB |
| msbB-N20 | atgtcgacgccccagccatg | Identification |
| pTA-PCR identification-R | ctctagcttcccggcaac | PTAT-msbB-RFP |

pTA vector construction. The genome of *Salmonella* VNP20009 strain is with aadA gene expressing streptomycin adenylyltransferase, and it is necessary to substitute the aadA resistance gene of pTargetF with a suitable resistance gene as a screening marker. The pTargetT-msbB-RFP constructed in this experiment (sequence not shown) could not work in *Salmonella* VNP20009, indicating that not all plasmids designed and constructed can work, but require experimental screening. The pTargetF resistance gene, aadA, was substituted with AmpR. Primers pT V-F/pT V-R were used for vectorPCRamplification with pTargetF as the template, and primers pT amp-F/pT amp-R were used for AmpR PCR amplification with pET-22b(+) as the template. The above two linear DNA fragments were recovered and purified from the gels, and then subjected to ligation at 37° C. for 30 min by one-step homologous recombination (based on the DNA ligation conditions). The recombinant products after DH5a transformation were taken and coated to an Amp+-resistant plate and subjected to inverted incubation overnight at 37° C. Monoclones were selected and verified.

Construction of pTAT-msbB-RFP plasmid (see sequence 2 in the Sequence Listing). The construction method is shown in FIG. 1. Primers pTargetF-msbB-R (P1)/pTA-vector-R (P10) were used for pTAT vector backbone PCR amplication with the pTA plasmid as the template; primers pTargetF-msbB-F (P2)/pTA-vector-F (P3) were used for msbB-sgRNA amplication with the pTA plasmid as the template; primers pTA-RFP-up-F (P4)/RFP-msbB-up-R (P5) were used for amplification of the upstream homology arm 678 bp of the msbB locus with the *Salmonella* VNP20009 genome as the template; primers RFP-msbB-middle-F (P6)/RFP-msbB-middle-R (P7) were used for RFP-ORF amplication with the synthetic TagRFP fragment as the template; primers RFP-msbB-down-F (P8)/pTA-RFP-down-R (P9) were used for amplification of the downstream homology arm 587 bp of the msbB locus with the *Salmonella* VNP20009 genome as the template. The above five linear DNA fragments were recovered and purified from the gels, and then subjected to ligation at 37° C. for 30 min by one-step homologous recombination (based on the DNA ligation conditions). The recombinant products after DH5a transformation were taken and coated to an Amp+-resistant plate and subjected to inverted incubation overnight at 37° C. Monoclones were selected and verified. The verification primer was msbB-N20/pTA-PCR identification-R, and the positive clone PCR band was 2770 bp.

Figure 2:
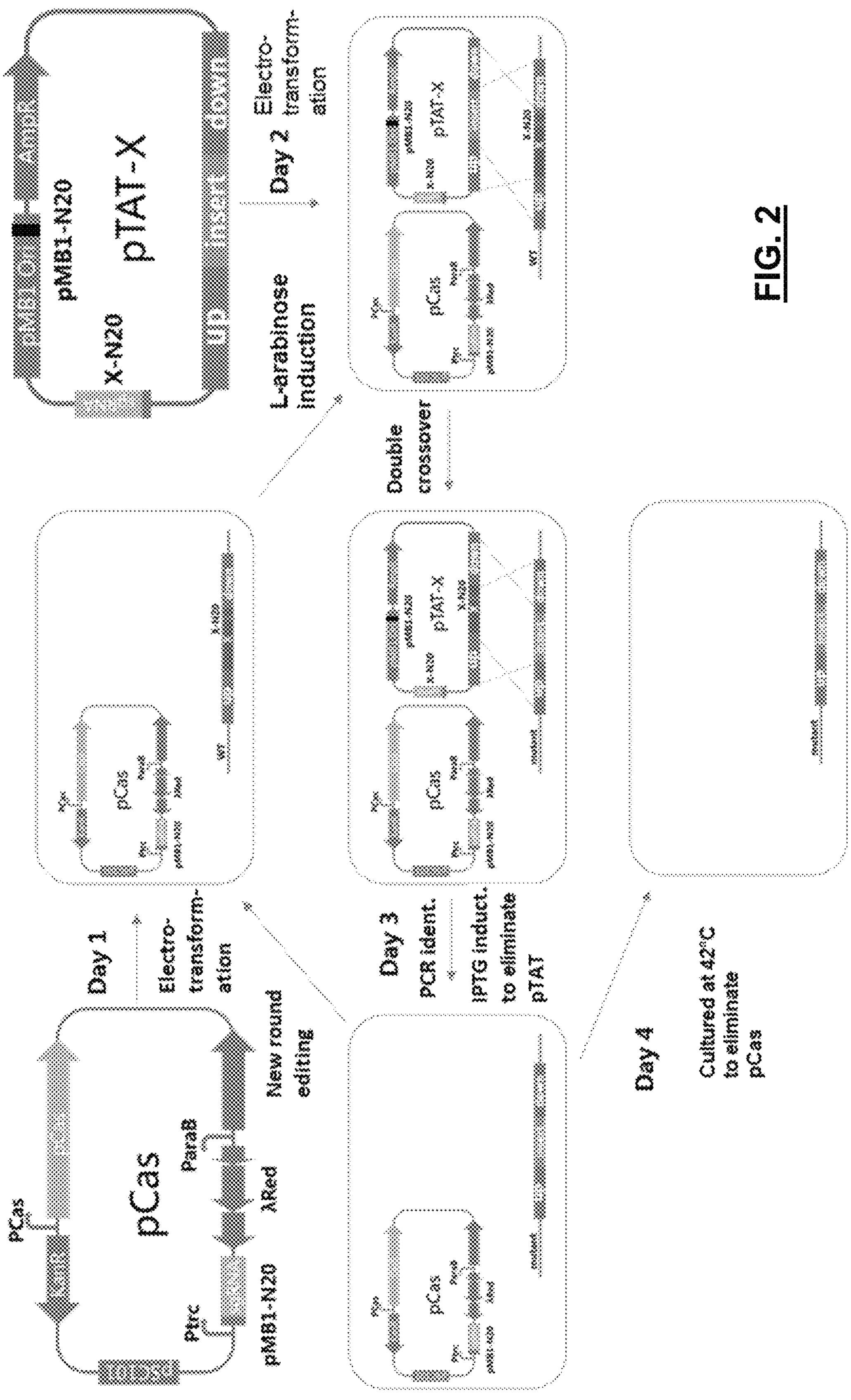
FIG. 2 shows a flowchart of the efficient and scarless gene editing system for *Salmonella* of the present invention.

Example 3 Substitution of the *Salmonella* VNP20009 msbB Locus with the RFP Gene The flowchart for the application of the efficient and traceless *Salmonella* gene editing system is shown in FIG. 2. On the first day pCas plasmid is transferred to *Salmonella*, and the resulting strains from this step can be conserved for editing of a series of target genes. On the second day, the pCas-*Salmonella* competence is prepared by adding L-arabinose to induce expression of the A-Red recombinase, followed by transfection of the pTAT-X plasmid and coating of Kan+/Amp+ plates. The homologous template in the positive clone is double crossover with the target gene, and the wild-type clone is subjected to X-N20 sgRNA-mediated Cas9 sustained cleavage of the double-stranded DNA, resulting in difficulty in growth of the wild strain. On the third day, monoclones are picked to identify the effect of genome editing, and the clones with successful editing are added to IPTG to induce pMB1-N20 sgRNA expression targeting the replicon of the pTAT-X plasmid, and the pTAT plasmid was removed. If a multi-gene modification is required, the strain obtained in this step contains the pCas plasmid and can be further used as a host bacteria for other gene modifications for a new round of editing. On the fourth day, the pCas plasmid is removed by incubation at 42° C. The primers used in this Example are shown in Table 6:

TABLE 6

| Primer | Sequence (5'-3') |
|---|---|
| pCas-identification-F | cagcttacatggcccaggtg |
| pCas-identification -R | aattcgtgtcgctcaaggcg |
| msbB-RFP-identification-F | gcgatccggagctggttg |
| msbB-RFP-identification-R | gcgagatgctggatggca |

pCas plasmid electrotransformed *Salmonella* VNP20009. *Salmonella* VNP20009 competence was prepared as described in Materials and Method 6. 1 μg of pCas plasmid was added to *Salmonella* VNP20009 competence, and after electrotransformation, it was resuscitated in antibiotic-free LB at 30° C. for 1 hour, then coated on Kan+-resistant LB plate, and subjected to inverted incubation at 30° C. overnight. Monoclones were picked and incubated at 30° C. to preserve the seed, and pCas-VNP20009 (pCas-VNP) strain was obtained. The verification primers were pCas-identification-F/pCas-identification-R, and the positive colony band containing pCas plasmid was 765 bp.

Preparation of *Salmonella* pCas-VNP20009 competence. 1) The *Salmonella* pCas-VNP strains obtained by electrotransformation were selected, plate streaking in Kan+-resistant LB, and incubate at 30° C. overnight. 2) The monoclines were picked and incubated in Kan+LB medium with shaking, and arabinose (10 mM final concentration) was added when $OD_{600}$ was about 0.2-0.3 to induce expression of Red recombinase. 3) When $OD_{600}$ was about 0.6-0.8, centrifuged at 5000 g for 4 min to collect the bacteria. 4) Washed with 10% glycerol for 3 times, the number of bacteria in each tube was adjusted to $1\times10^9$ CFU, and finally the bacteria were resuspended in 80 μL of 10% glycerol.

The pTAT-msbB-RFP plasmid electrotransformed *Salmonella* pCas-VNP. 1 μg pTAT-msbB-RFP plasmid was added to *Salmonella* pCas-VNP competence, and after electrotransformation, it was resuscitated for 1 hr at 30° C. in antibiotic-free LB, coated on Kan+/Amp+-resistant LB plates, and then subjected to inverted incubation at 30° C. overnight.

msbB site RFP substitution verification. A number of monoclonal clones on the above Kan+/Amp+-resistant LB plates, and *Salmonella* VNP20009 wild type (WT) clone was used as a negative control, and the colonies were subjected to agarose gel electrophoresis after PCR using the primers msbB-RFP-identification-F/msbB-RFP-identification-R. The positive band for successful knock-in was 2475 bp and the negative band for unsuccessful knock-in or WT was 1931 bp. Editing efficiency=number of positive colonies/total number of colonies×100%.

Figure 3:
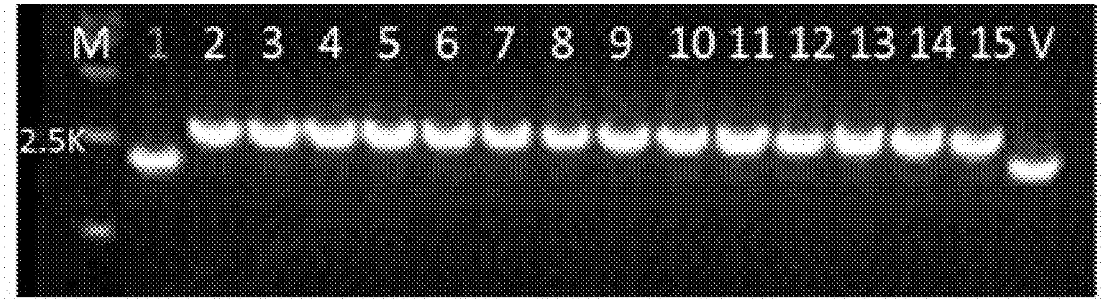
FIG. 3 shows agarose gel electrophoresis of the PCR amplification products of the *Salmonella* VNP20009 with msbB locus substituted by RFP of the present invention, wherein 1-15 are *Salmonella* in the experimental group; V is control *Salmonella*; and M is DNA molecular weight Marker.

The results of the msbB site RFP substitution are shown in FIG. 3. 14 of the 15 monoclones were knocked in successfully and 1 failed, with an editing efficiency being 93.3%.

Elimination of pTAT plasmid. The clones verified to be knocked-in successfully were transferred to 3 ml Kan+LB medium, and IPTG (final concentration 0.5 mM) was added and incubated at 30° C. for 8 h. The sgRNA expression targeting the pTAT replicon was induced, and in combination with Cas9 to cause the DNA double-strand break at the PTAT plasmid replicon. The cultured bacteria solutions on the Kan+/Amp+-resistant LB plate and Kan+-resistant LB plates were streaked. The pTAT plasmid has been eliminated if no *Salmonella* clone grows from the double-resistant plate, and if it is found that some *Salmonella* clones grow, it is again transferred to a Kan+LB medium containing IPTG. Some monoclones were selected from the Kan+-resistant plate and blown and mixed well in 10 μL of sterile water, and 5 μL was added to Kan+LB and Kan+/Amp+LB respectively. pTAT plasmid elimination was confirmed by the growth of *Salmonella* clones only in Kan+LB. Several *Salmonella* monoclones grown on Kan+ plates after IPTG induction can also be directly identified by PCR, e.g., using the primer pTA-PCR identification-R/RFP-msbB-down-F, and using *Salmonella* clones without elimination of pTAT as a positive control. If no band is identified by PCR, it indicates that the pTAT plasmid has been removed.

Elimination of pCas plasmid. The *Salmonella* clones after elimination of the pTAT plasmid were transferred to the antibiotic-free LB and incubated at 42° C. for 8 h. The bacteria solution was streaked on the antibiotic-free LB plate, and *Salmonella* monoclones were selected and transferred to the Kan+ or antibiotic-free LB, and the *Salmonella* clones that did not grow in the Kan+LB were considered to be successful in elimination of pCas.

Bacterial growth curve and fluorescence assay. Three clones with pTAT plasmid eliminated and three *Salmonella* clones containing pCas were selected and transferred to 3 mL Kan+LB and incubated overnight. 300 μL of Kan+LB medium was added to each well of the culture plate for Bioscreen automatic growth curve analyzer, and then 1 μL of the overnight culture solution was added, and incubate at 30° C. for 24 hr. The overnight culture solution was transferred to a 3 mL Kan+LB tube in a volume ratio of 1/1000 and incubated at 30° C. for 24 hr. The fluorescence intensity of RFP (excitation wavelength 550 nm, emission wavelength 590 nm) and $OD_{600}$ were measured by using TECAN Infinite M200 microplate reader.

Figure 4:
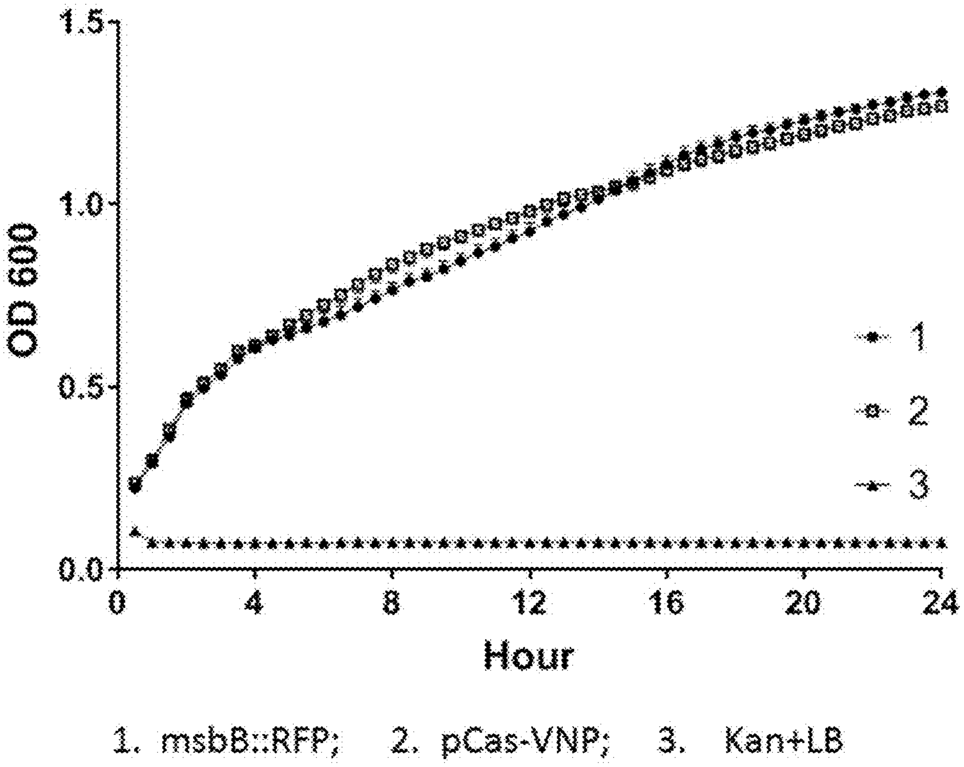
FIG. 4 shows the growth curve of the msbB strain of the present invention; pCas-VNP was used as a control. Three independent replicates, mean±SEM.

The growth curve of *Salmonella* msbB strain is shown in FIG. 4, and there is no significant difference between the growth curves of the successfully edited *Salmonella* clone msbB::RFP and *Salmonella* pCas-VNP, which indicates that the efficient and traceless *Salmonella* gene editing system of the present invention can achieve accurate positioning and design, and is free of off-target that may occur in CRISPR-Cas9. Three independent replicates, MEAN±SEM.

Figure 5:
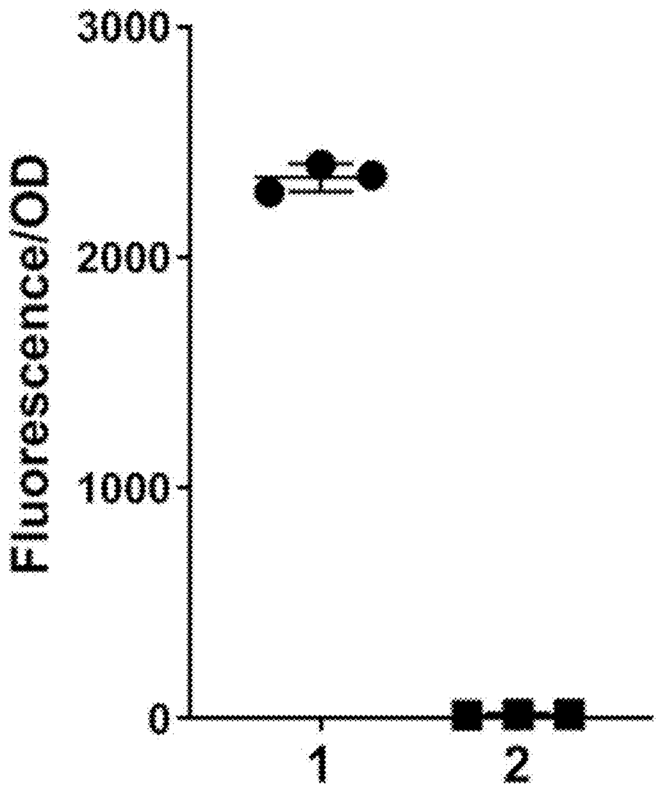
FIG. 5 shows the fluorescence intensity of the msbB strain of the present invention; pCas-VNP was used as a control. Three independent replicates, mean±SEM.

The fluorescence intensities of the *Salmonella* msbB strains are shown in FIG. 5. Significant fluorescence was detected for the successfully edited *Salmonella* clone msbB::RFP, and the fluorescence of *Salmonella* VNP20009 was essentially equivalent to that of the LB background. Fluorescence was calculated as (fluorescence-fluorescence$_{LB}$)/(OD-OD$_{LB}$). Three independent replicates, mean±SEM.

Example 4 Substitution of the *Salmonella* VNP20009 eutC Locus with the RFP Gene pTAT-eutC-RFP plasmid was constructed (see sequence 3). 636 bp in the eutC-ORF (CP007804.2, 2,508,639~2,509,274) was substituted with RFP-ORF. 5'-ggcgctgttgcgcttcctgg-3' was selected as eutC2-N20, and based on the selected N20 sequence, the primer pTA-eutC2-F (sequence: ggcgctgttgcctgccttcctgggttttagagagctagaaatagc) was designed to construct a targeting plasmid, so that sgRNA that can mediate Cas9 protein cleavage of the corresponding target sites of the msbB gene is expressed. Primers pTA-eutC2-R/pTA-vector-R were used for PCR amplification of the pTAT vector backbone, with the pTA plasmid as the template; primers pTA-eutC2-F/pTA-vector-F were used for amplification of the eutC2-sgRNA, with the pTA plasmid as the template; primers eutC2-plasmid template up-F/eutC2-up RFP-R were used for amplification of the upstream homology arm 301 bp of the eutC locus, with the *Salmonella* VNP20009 genome as the template; primers RFP-msbB-mid-F/RFP-msbB-mid-R were used for amplification of RFP-ORF, with the synthesized TagRFP fragment as the template; and primers eutC2-down RFP-F/eutC2-plasmid-template down-R were used for amplification of the downstream homology arm 304 bp of the eutC locus, with *Salmonella* VNP20009 genome as the template. The ligation step was the same as in Example 1. Verification primer was eutC2-N20/pTA-PCR identification-R, and the positive clone PCR band was 2110 bp. The primers used in this Example are shown in Table 7.

TABLE 7

| Primer | Sequence (5'-3') | Use |
|---|---|---|
| pTA-eutC2-R | ccaggaagcgcaacagcgccactagtattatacctaggac | pTA vector |
| pTA-vector-R | gcttagatctattaccctgttatcc | |
| pTA-eutC2-F | ggcgctgttgcgcttcctgggttttagagctagaaatagc | eutC2-sgRNA |
| pTA-vector-F | ttctgcaggtcgactctagagag | |
| eutC2-plasmid template upper-F | tctagagtcgacctgcagaactcaactaccagaccaccgc | eutC upstream homology arm |
| eutC2-upper RFP-R | agaattcttataagggatttccgtcggcgcggcgcgcact | |
| rfp-msbb-mid-f | gccgccatttttgcccaaatcccttataagaattctcacactgg | RFP-ORF |
| RFP-msbB-mid-R | ggctttttgggatcccagtgatggttaaccc | |
| eutC2-lower RFP-F | gttaaccatcactgggatccccgtcgaggccgacagaa | eutC downstream homology arm |
| eutC2-plasmid template lower-R | acagggtaatagatctaagctcagcggcaatataggtcac | |
| eutC2-N20 | ggcgctgttgcgcttcctgg | appraise |
| pTA-PCR identification-R | ctctagcttcccggcaac | PTAT-eutC2-RFP |

TABLE 7-continued

| Primer | Sequence (5'-3') | Use |
|---|---|---|
| eutC-RFP-identification-F | gtgaacaccgtggtgggc | Identification of eutC:: RFPs Substitution results |
| eutC-RFP-identification-R | gcgcgatacctgcggtag | |

The method of Preparation of *Salmonella* pCas-VNP competence was as described in Example 2.

The pTAT-eutC-RFP plasmid electrotransformation of *Salmonella* pCas-VNP was as described in Example 2.

Verification of eutC siteRFP substitution. The method was as described in Example 2. Primers eutC-RFP-identification-F/eutC-RFP-identification-R were used, and the positive band for successful knock-in was 1953 bp, and the negative band for unsuccessful knock-in or wild-type was 1750 bp.

Figure 6:
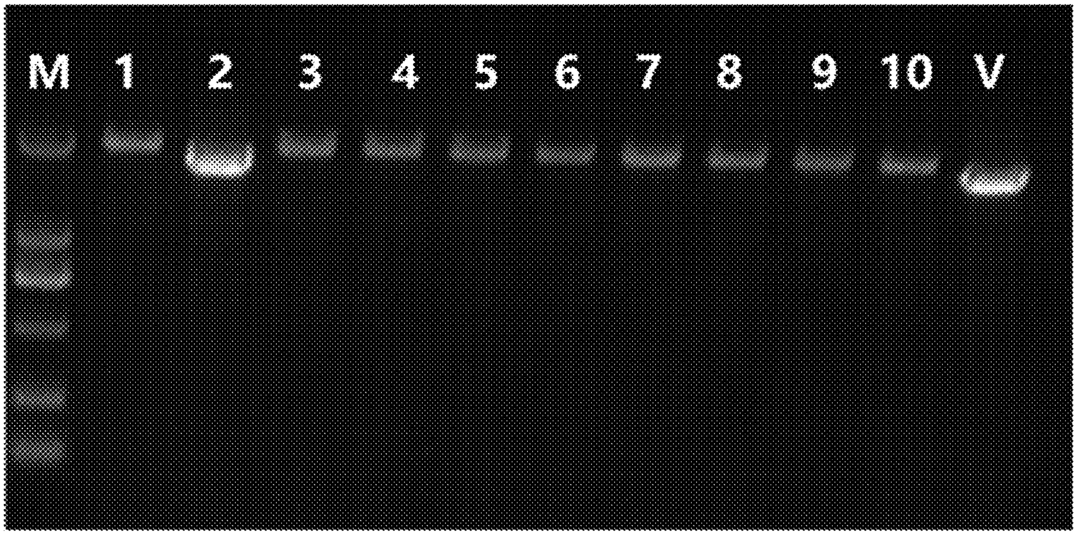
FIG. 6 shows the agarose gel electrophoresis of the PCR amplification products of the *Salmonella* VNP20009 with eutC locus substituted by RFP of the present invention; wherein, 1 to 10 are *Salmonella* in the experimental group; V is control *Salmonella*; and M is the DNA molecular weight Marker DL2000, with the bands being 2000, 1000, 750, 500, 250, and 100 bp, respectively.

The results of RFP substitution for the eutC locus are shown in FIG. 6, with 9 out of 10 monoclones knocked in successfully and 1 failed, editing efficiency 90%.

The methods of eliminating the pTAT-eutC-RFP plasmid and the pCas plasmid were as described in Example 2.

Figure 7:
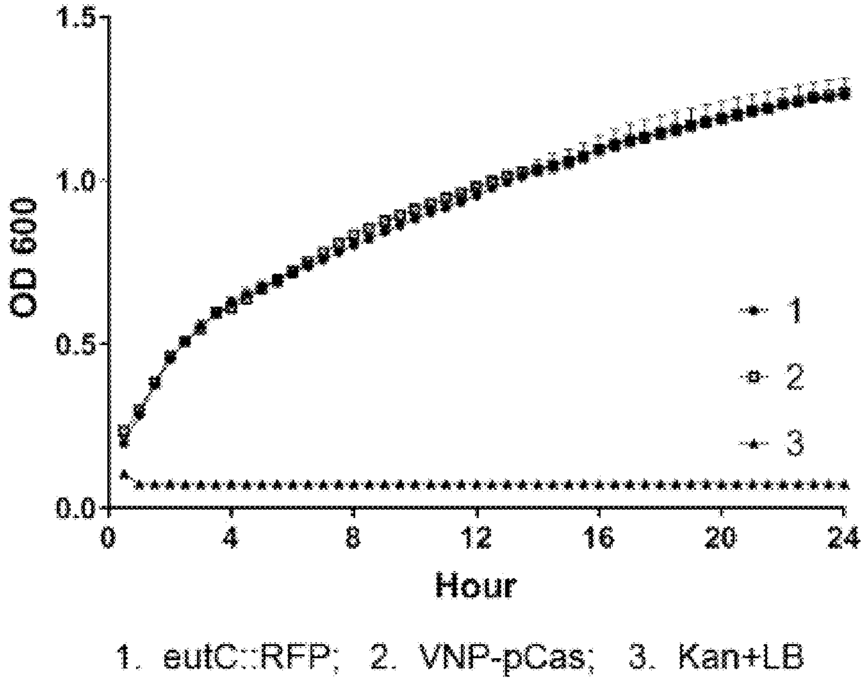
FIG. 7 shows the growth curve of the eutC strain of the present invention; pCas-VNP was used as a control. Three independent replicates, mean±SEM.

The growth curve of eutC strain are shown in FIG. 7. There is no significant difference between the growth curves of the successfully edited *Salmonella* clone eutC::RFP and *Salmonella* pCas-VNP, which indicates that the efficient and traceless *Salmonella* gene editing system of the present invention can achieve accurate positioning and design, and is free of off-target that may occur in CRISPR-Cas9. Three independent replicates, MEAN±SEM.

Figure 8:
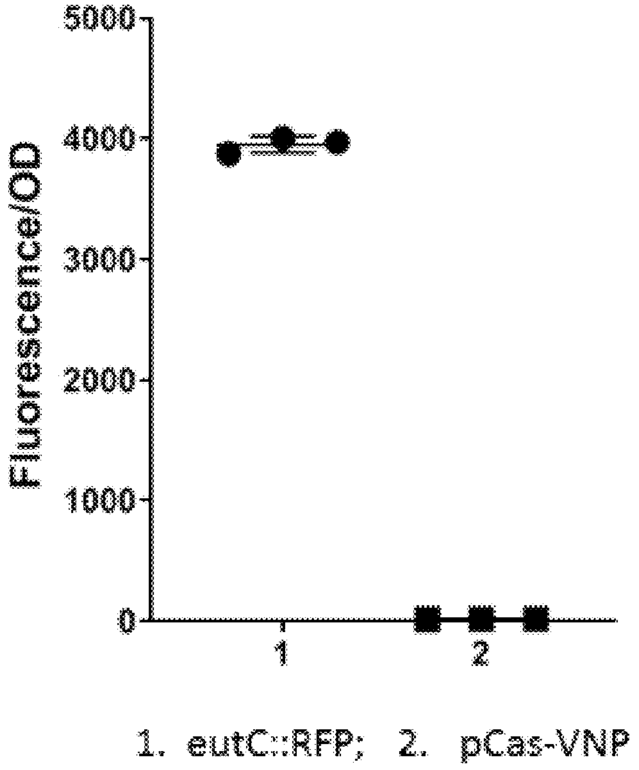
FIG. 8 shows the fluorescence intensity of the eutC strain of the present invention; pCas-VNP was used as a control. Three independent replicates, mean±SEM.

The fluorescence intensity of the eutC strains are shown in FIG. 8. Significant fluorescence was detected for the successfully edited *Salmonella* clone eutC::RFP, and the fluorescence of *Salmonella* VNP20009 was essentially equivalent to that of the LB background. Fluorescence was calculated as (fluorescence-fluorescence$_{LB}$)/(OD-OD$_{LB}$). Three independent replicates, mean±SEM.

Example 5 Evaluation of Gene-Edited *Salmonella* VNP20009 eutC for Antitumor Applications The B16F10 melanoma mouse model was constructed. B16F10 mouse melanoma cells were grown in DMEM cell culture medium until the exponential growth phase and then digested with 0.5% pancreatin, followed by centrifugation at 1000 rpm/min for 3 min, and the supernatant culture medium was removed and washed twice with PBS for cell counting, and the cells were finally resuspended in PBS to adjust the final concentration of cells to $2\times10^6$ cells/mL. Each C57BL/6 mouse was inoculated with 100 μL of cells at the axillary fat pad of the mouse, i.e., $2\times10^5$ cells per mouse. After inoculation, the mice were raised in a clean-grade animal house, and the subsequent experiments were performed when the tumor volume of the mice grew to approximately 150 mm$^3$.

The anti-tumor effect of the modified strains were evaluated. Plasmid-free *Salmonella* VNP20009-msbB::RFP (msbB) and *Salmonella* VNP20009-eutC::RFP (eutC) strains were subjected to plate streaking on an antibiotic-free LB plate and incubated overnight at 37° C., and the *Salmonella* monoclones were picked off and transferred to 3 mL of LB for resuscitation, and then transferred to 3 ml of LB and incubated until the OD value was about 0.8, and subsequently centrifuged at 5000 g for 3 min to collect the bacteria, washed twice with sterile PBS, and then resuspended in PBS to adjust the final concentration to $1\times10^6$ cfu/mL. 22 tumor-bearing mice were then taken and randomly divided into 3 groups (6 mice in the PBS group, and 8 mice in the msbB or eutC groups), and the mice in the msbB and eutC groups were intraperitoneally injected with 100 μL of the *Salmonella* msbB strains and *Salmonella* eutC strains, i.e., $1\times10^5$ cfu, respectively. The PBS group was intraperitoneally injected with 100 μL of PBS. Tumor size and survival status of the mice were recorded continuously.

Figure 9:
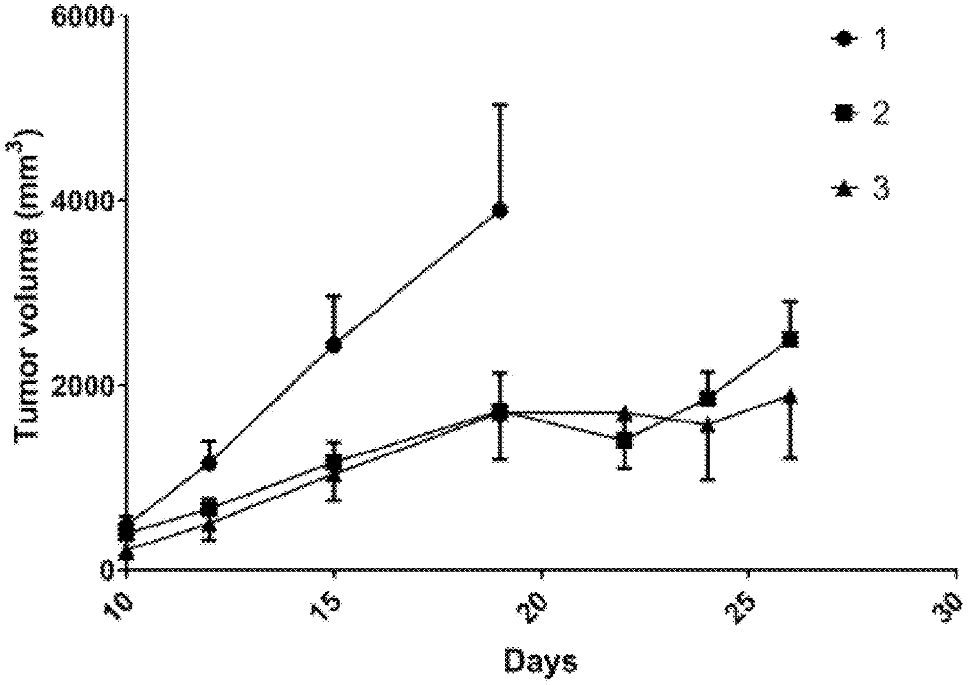
FIG. 9 shows the respective tumor growth curves of the tumor-bearing mice in the eutC: RFP group, msbB::RFP group and PBS blank group of the present invention.

The tumor growth curves of the tumor-bearing mice are shown in FIG. 9. There was no significant difference in tumor size between the *Salmonella* eutC group and the *Salmonella* msbB group, indicating that lack of the eutC gene had no significant effect on the antitumor effect of *Salmonella* VNP20009, which verified the results of the bacterial growth in vitro. However, the *Salmonella* experimental group had a significant antitumor effect compared to the negative PBS control.

Figure 10:
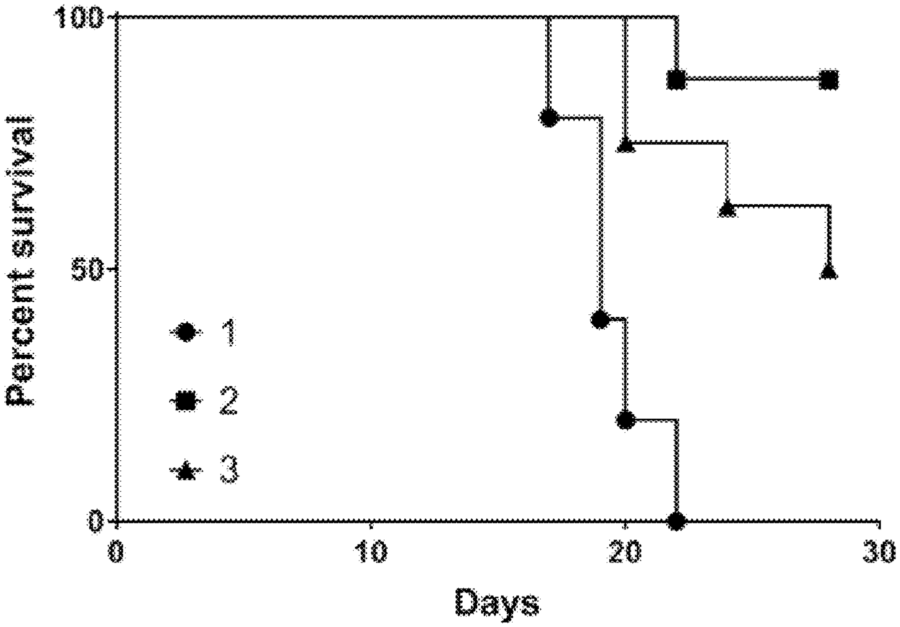
FIG. 10 shows the respective survival curves of the tumor-bearing mice in the eutC::RFP group, msbB::RFP group and PBS blank group of the present invention.

The survival curves of the tumor-bearing mice are shown in FIG. 10. Mice in the *Salmonella* eutC group had significantly longer survival time than the *Salmonella* msbB group ($P<0.05$), and both *Salmonella* groups had significantly longer mouse survival time than the PBS group. The results of significant prolongation of survival time of mice in the *Salmonella* eutC group compared to the *Salmonella* msbB group are significantly different from the results of in vitro bacterial growth as well as from the results of FIG. 9, indicating that the *Salmonella* eutC produced by the technology of the invented efficient and traceless gene editing system for *Salmonella* has a promising application in the preparation of antitumor drugs.

Utilizing the technology of an efficient and traceless gene editing system for *Salmonella* of the present invention, 8 different target sites/target genes evenly distributed on the chromosome around the replication initiation site of the *Salmonella* chromosome were selected, which are located at positions 245,209, 1,290,176, 1,886,549, 2,509,349, 3,299,845, 3,988,068, 3,996,444, 4,483,494 bp of the bacterial chromosome, and the editing efficiencies were all above 90%, thereby systematically verifying the high efficiency of the invented efficient and traceless gene editing system for *Salmonella* in *Salmonella* gene editing.

The above description shows and describes the basic principle, main features and advantages of the present invention. One skilled in the art should understand that the present invention is not limited by the above embodiments, and what is described in the above embodiments and the specification is only to illustrate the principle of the present invention, and there will be various changes and improvements to the present invention without departing from the spirit and scope thereof. The scope of the present invention is defined by the appended claims, specification and the equivalents thereof.

What is claimed is:

1. An efficient and traceless gene editing system for *Salmonella*, wherein the efficient and traceless gene editing system for *Salmonella* consists of a dual plasmid CRISPR/Cas9 system comprising a helper plasmid A expressing a relevant functional protein and a targeting plasmid B expressing a target site sgRNA, wherein the target site is within *Salmonella*, and wherein the targeting plasmid B comprises a targeting plasmid screening marker gene, and the targeting plasmid screening marker gene is AmpR, and the targeting plasmid B is constructed by one-step homologous recombination.

2. The efficient and traceless gene editing system for *Salmonella* according to claim 1, wherein the helper plasmid A comprises nucleic acid sequences of components: a Cas9 protein, a λRed recombinase, a temperature-sensitive replicon, an sgRNA expression frame of the targeting plasmid B replicon, and a helper plasmid A screening marker gene, and wherein the recombinase and sgRNA are inducibly expressed.

3. The efficient and traceless gene editing system for *Salmonella* according to claim 2, wherein the targeting plasmid B further comprises nucleic acid sequences of components: a replicon, an sgRNA expression frame for a target site, and a DNA fragment for homologous recombination, and wherein the replicons of the helper plasmid A and the targeting plasmid B are cabable of being replicated in *Escherichia coli* and *Salmonella*, the replicon and the screening marker gene of the plasmid B are different from the replicon and the screening marker gene of the plasmid A, and the replicon of the targeting plasmid B is compatible with the replicon of the helper plasmid A.

4. The efficient and traceless gene editing system for *Salmonella* according to claim 3, wherein the sgRNA expression frame has a promoter-(N)X-sgRNA backbone-terminator structure, and the target site DNA has a 5'-(N)X-NGG-3' structure, and wherein (N)X denotes X Ns, N is any of the bases A, T, C or T, and X is an integer greater than 15 and less than 25.

5. The efficient and traceless gene editing system for *Salmonella* according to claim 4, wherein the X of the target site DNA is 20, and the homologous recombinant DNA fragment is upstream homology arm-insert fragment-downstream homology arm when used for knock-in or substitution, and upstream homology arm-downstream homology arm when used for knock-out; the DNA fragment is constructed in the targeting plasmid B or in a PCR product; and the gene editing system is capable of gene editing on multiple target sites simultaneously.

6. The efficient and traceless gene editing system for *Salmonella* according to claim 5, wherein the targeting plasmid B comprises editing modules for multiple target sites with a structure of plasmid backbone (resistance gene-replicon)-editing module 1 (target site 1 sgRNA expression frame-upstream homology arm 1-knock-in (or substitution) fragment-downstream homology arm 1)-editing module 2 (target site 2 sgRNA expression frame-upstream homology arm 2-knock-in (or substitution) fragment-downstream homology arm 2)-editing module n, and the number of target sites is not greater than 3.

7. A method of constructing the targeting plasmid B according to claim 1, comprising the following steps:

1) for knock-in (or substitution): amplifying the targeting plasmid B backbone, the target site sgRNA expression frame, the upstream/downstream homology arms, and the knock-in (or substitution) fragment, respectively, and ligating all DNA fragments using one-step homologous recombination; or
2) for knock-out: amplifying the targeting plasmid B backbone, the target site sgRNA expression frame, and the upstream/downstream homology arms, respectively, and ligating all DNA fragments using one-step homologous recombination; or 3) for targeting plasmid B containing in no homology arms, amplifying the upstream/downstream homology arms respectively, and ligating them as a linear DNA template.

8. A method for using the efficient traceless gene editing system according to claim 1 for *Salmonella* in genome editing, comprising the following steps:

1) introducing the helper plasmid A into *Salmonella* and inducing a λRed recombinase expression to prepare competent cells;

2) introducing the targeting plasmid B and a linear DNA template to the competent cells of step 1), or introducing a targeting plasmid B comprising the template DNA;

3) resuscitating the cells from step 2) and coating on a plate comprising two resistances corresponding respectively to the plasmid A and the plasmid B, and screening for positive clones with double crossover;

4) after performing PCR or sequencing verification of the positive clones, inducing sgRNA expression of the targeting plasmid B replicon and eliminating the plasmid B;

5) after verifying the elimination of the plasmid B, increasing the bacterial culture temperature and eliminating the plasmid A to obtain a successfully modified *Salmonella* clone.

9. The method for using the efficient traceless gene editing system for *Salmonella* in genome editing according to claim 8, wherein at the end of step 4), the plasmid A is retained, and step 2) is repeated to introduce the targeting plasmid B and a template DNA for targeting other loci.

10. The use of the efficient traceless gene editing system for *Salmonella* in genome editing according to claim 8, wherein the successfully modified *Salmonella* is an eutC gene-deficient *Salmonella*.

11. The use of the efficient traceless gene editing system for *Salmonella* in genome editing according to claim 8, wherein the eutC gene-deficient *Salmonella* is used to prepare *Salmonella* antitumor drugs.

* * * * *

SEQUENCE LISTING

<160> NUMBER OF SEQ ID NOS: 3

<210> SEQ ID NO 1
<211> LENGTH: 1073
<212> TYPE: DNA
<213> ORGANISM: Artificial sequence
<220> FEATURE:
<223> OTHER INFORMATION: synthesized

<400> SEQUENCE: 1

```
aaatccctta taagaattct cacactggct caccttcggg tgggcctttc tgcgtttata      60
tactagagag agaatataaa aagccagatt attaatccgg ctttttttatt atttaggtga    120
tccatcgaac tctagaattt gacggctagc tcagtcctag gtacagtgct agcctagata    180
ctagagaaag aggagaaata ctagatggtt agcaaaggcg aagagctgat caaggagaac    240
atgcacatga aactgtacat ggaaggtacc gttaacaacc accattttaa gtgcaccagc    300
gaaggcgagg gtaaaccgta tgagggcacc cagaccatgc gtatcaaggt ggttgaaggt    360
ggcccgctgc cgtttgcgtt cgatattctg gcgaccagct ttatgtacgg cagccgtacc    420
ttcatcaacc atacccaggg tattccggat ttctttaaac agagctttcc ggagggcttc    480
acctgggaac gtgtgaccac ctacgaggac ggtggcgttc tgaccgcgac ccaggatacc    540
agcctgcaag acggttgcct gatctataac gtgaaaattc gtggcgttaa ctttccgagc    600
aacggtccgg tgatgcagaa aaagaccctg ggctgggaag cgaacaccga gatgctgtac    660
ccggcggatg gtggcctgga aggtcgtagc gacatggcgc tgaagctggt tggtggcggt    720
cacctgatct gcaacttcaa aaccacctat cgtagcaaaa agccggcgaa aaacctgaag    780
atgccgggcg tgtactatgt tgatcatcgt ctggaacgta ttaaagaggc ggacaaggaa    840
acctacgtgg aacagcacga ggtggcggtt gcgcgttatt gcgacctgcc gagcaaactg    900
ggtcataagc tgaactaacc aggcatcaaa taaaacgaaa ggctcagtcg aaagactggg    960
cctttcgttt tatctgttgt ttgtcggtga acgctctcta ctagagtcac actggctcac   1020
cttcgggtgg gcctttctgc gtttataagc tgggttaacc atcactggga tcc          1073
```

<210> SEQ ID NO 2
<211> LENGTH: 4511
<212> TYPE: DNA
<213> ORGANISM: Artificial sequence
<220> FEATURE:
<223> OTHER INFORMATION: synthesized

<400> SEQUENCE: 2

```
tcgagttacc aatgcttaat cagtgaggca cctatctcag cgatctgtct atttcgttca      60
tccatagttg cctgactccc cgtcgtgtag ataactacga tacgggaggg cttaccatct    120
ggccccagtg ctgcaatgat accgcgagac ccacgctcac cggctccaga tttatcagca    180
ataaaccagc cagccggaag ggccgagcgc agaagtggtc ctgcaacttt atccgcctcc    240
atccagtcta ttaattgttg ccgggaagct agagtaagta gttcgccagt taatagtttg    300
cgcaacgttg ttgccattgc tacaggcatc gtggtgtcac gctcgtcgtt tggtatggct    360
tcattcagct ccggttccca acgatcaagg cgagttacat gatcccccat gttgtgcaaa    420
aaagcggtta gctccttcgg tcctccgatc gttgtcagaa gtaagttggc cgcagtgtta    480
tcactcatgg ttatggcagc actgcataat tctcttactg tcatgccatc cgtaagatgc    540
ttttctgtga ctggtgagta ctcaaccaag tcattctgag aatagtgtat gcggcgaccg    600
agttgctctt gcccggcgtc aatacgggat aataccgcgc cacatagcag aactttaaaa    660
```

```
gtgctcatca ttggaaaacg ttcttcgggg cgaaaactct caaggatctt accgctgttg    720
agatccagtt cgatgtaacc cactcgtgca cccaactgat cttcagcatc ttttactttc    780
accagcgttt ctgggtgagc aaaaacagga aggcaaaatg ccgcaaaaaa gggaataagg    840
gcgacacgga aatgttgaat actcatactc ttcctttttc aatattattg aagcatttat    900
cagggttatt gtctcatgag cggatacata tttgaatgta tttagaaaaa taaacaaata    960
ggggttccgc gatgccgctc gccagtcgat tggctgagct catgaagttc ctattccgaa   1020
gttccgcgaa cgcgtaaagg atctaggtga agatcctttt tgataatctc atgaccaaaa   1080
tcccttaacg tgagttttcg ttccactgag cgtcagaccc cgtagaaaag atcaaaggat   1140
cttcttgaga tccttttttt ctgcgcgtaa tctgctgctt gcaaacaaaa aaaccaccgc   1200
taccagcggt ggtttgtttg ccggatcaag agctaccaac tctttttccg aaggtaactg   1260
gcttcagcag agcgcagata ccaaatactg tccttctagt gtagccgtag ttaggccacc   1320
acttcaagaa ctctgtagca ccgcctacat acctcgctct gctaatcctg ttaccagtgg   1380
ctgctgccag tggcgataag tcgtgtctta ccgggttgga ctcaagacga tagttaccgg   1440
ataaggcgca gcggtcgggc tgaacggggg gttcgtgcac acagcccagc ttggagcgaa   1500
cgacctacac cgaactgaga tacctacagc gtgagctatg agaaagcgcc acgcttcccg   1560
aagggagaaa ggcggacagg tatccggtaa gcggcagggt cggaacagga gagcgcacga   1620
gggagcttcc agggggaaac gcctggtatc tttatagtcc tgtcgggttt cgccacctct   1680
gacttgagcg tcgatttttg tgatgctcgt caggggggcg gagcctatgg aaaaacgcca   1740
gcaacgcggc ctttttacgg ttcctggcct tttgctggcc ttttgctcac atgttctttc   1800
ctgcgttatc ccctgattct gtggataacc gtattaccgc ctttgagtga gctgataccg   1860
ctcgccgcag ccgaacgacc gagcgcagcg agtcagtgag cgaggaagcg gaagagcgcc   1920
tgatgcggta ttttctcctt acgcatctgt gcggtatttc acaccgcata tgctggatcc   1980
ttgacagcta gctcagtcct aggtataata ctagtatgtc gacgccccag ccatggtttt   2040
agagctagaa atagcaagtt aaaataaggc tagtccgtta tcaacttgaa aaagtggcac   2100
cgagtcggtg ctttttttga attctctaga gtcgacctgc agaacatcac cgcaacgcaa   2160
atgatggagt cgatgatcac caacccgatg ccgacccgtg cggaagtgat ggacgtggcg   2220
aacgccgtcc tggatggcac ggatgcggtt atgctgtctg ccgaaaccgc agccggtcag   2280
tatccttctg aaaccgttgc cgcaatggcg cgcgtctgcc tgggcgcaga aaaaatcccc   2340
agcatcaatg tgtctaaaca ccgtctcgac gtgcagttcg acaacgttga agaagccatt   2400
gccatgtctg cgatgtatgc ggcaaaccat ctgaaaggcg ttaccgcgat catcaccatg   2460
acggaatccg gtcgtaccgc gctaatgact tcccgtatca gctccggcct gccgattttc   2520
gccatgtcgc gccatgaacg cacgctgaac ctgaccgcgc tctatcgcgg agtaacgccg   2580
gtgcattttg atagcgcggc tgatggcgtt gtcgcggcac atgaagctgt taatctgctg   2640
cgcgataaag ggtatctggt ttccggcgac ctggttatcg tgacccaggg cgatgtcatg   2700
agcaccgtcg gttcaaccaa taccacgcgc aaacgtccgc cgaaacgccg acgcactgtg   2760
ttccagatat agtcaaaaac cggattaccc tgattatgaa acatcgccgc catttttttgc   2820
ccaaatccct tataagaatt ctcacactgg ctcaccttcg ggtgggcctt tctgcgttta   2880
tatactagag agagaatata aaaagccaga ttattaatcc ggcttttttta ttatttaggt   2940
gatccatcga actctagaat ttgacggcta gctcagtcct aggtacagtg ctagcctaga   3000
```

```
tactagagaa agaggagaaa tactagatgg ttagcaaagg cgaagagctg atcaaggaga   3060
acatgcacat gaaactgtac atggaaggta ccgttaacaa ccaccatttt aagtgcacca   3120
gcgaaggcga gggtaaaccg tatgagggca cccagaccat gcgtatcaag gtggttgaag   3180
gtggcccgct gccgtttgcg ttcgatattc tggcgaccag ctttatgtac ggcagccgta   3240
ccttcatcaa ccatacccag ggtattccgg atttctttaa acagagcttt ccggagggct   3300
tcacctggga acgtgtgacc acctacgagg acggtggcgt tctgaccgcg acccaggata   3360
ccagcctgca agacggttgc ctgatctata acgtgaaaat tcgtggcgtt aactttccga   3420
gcaacggtcc ggtgatgcag aaaaagaccc tgggctggga agcgaacacc gagatgctgt   3480
acccggcgga tggtggcctg gaaggtcgta gcgacatggc gctgaagctg gttggtggcg   3540
gtcacctgat ctgcaacttc aaaaccacct atcgtagcaa aaagccggcg aaaaacctga   3600
agatgccggg cgtgtactat gttgatcatc gtctggaacg tattaaagag gcggacaagg   3660
aaacctacgt ggaacagcac gaggtggcgg ttgcgcgtta ttgcgacctg ccgagcaaac   3720
tgggtcataa gctgaactaa ccaggcatca aataaaacga aaggctcagt cgaaagactg   3780
ggcctttcgt tttatctgtt gtttgtcggt gaacgctctc tactagagtc acactggctc   3840
accttcgggt gggcctttct gcgtttataa gctgggttaa ccatcactgg gatcccaaaa   3900
aagccggcac acatcgcgta ccggctctgt cagcgcattt gttaatcgaa gcgcagttgc   3960
ggcagaacct ctttcacctg tgccaggtat tcacgacgat ctgaccccgt cagaccttcc   4020
gtgcgcggca attttgctgt cagagggtta acggcttgct ggttgatcca tacctcataa   4080
tgcagatgcg gccctgtgga acgcccggtg ttaccagaaa gcgcaatacg atcgccacgt   4140
ttcacttttt gccccggttt caccagcagc ttacgcaagt gcatgtaacg tgtggtgtag   4200
gtgcgtccat gacgaatcgc aatgtagtaa ccggcagcgc cgctacgttt agcgaccacg   4260
acctcgccat cccccaccga cagcaccggc gtaccctgcg gcatcgcaaa gtcaacgcca   4320
cgatgcggcg caacgcgtcc ggtaaccggg ttcagacgac gcggattgaa gttggaggag   4380
atgcggaact gtttagcggt cgggaagcgt aaaaagcctt tcgccagacc aaccccatta   4440
cggtcataga atttaccgtc agcggcgcga atggcgtagt aagcttagat ctattaccct   4500
gttatcccta c                                                        4511
```

<210> SEQ ID NO 3
<211> LENGTH: 3851
<212> TYPE: DNA
<213> ORGANISM: Artificial sequence
<220> FEATURE:
<223> OTHER INFORMATION: synthesized

<400> SEQUENCE: 3

```
tcgagttacc aatgcttaat cagtgaggca cctatctcag cgatctgtct atttcgttca     60
tccatagttg cctgactccc cgtcgtgtag ataactacga tacgggaggg cttaccatct    120
ggccccagtg ctgcaatgat accgcgagac ccacgctcac cggctccaga tttatcagca    180
ataaaccagc cagccggaag ggccgagcgc agaagtggtc ctgcaacttt atccgcctcc    240
atccagtcta ttaattgttg ccgggaagct agagtaagta gttcgccagt taatagtttg    300
cgcaacgttg ttgccattgc tacaggcatc gtggtgtcac gctcgtcgtt tggtatggct    360
tcattcagct ccggttccca acgatcaagg cgagttacat gatcccccat gttgtgcaaa    420
aaagcggtta gctccttcgg tcctccgatc gttgtcagaa gtaagttggc cgcagtgtta    480
tcactcatgg ttatggcagc actgcataat tctcttactg tcatgccatc cgtaagatgc    540
```

```
ttttctgtga ctggtgagta ctcaaccaag tcattctgag aatagtgtat gcggcgaccg    600
agttgctctt gcccggcgtc aatacgggat aataccgcgc cacatagcag aactttaaaa    660
gtgctcatca ttggaaaacg ttcttcgggg cgaaaactct caaggatctt accgctgttg    720
agatccagtt cgatgtaacc cactcgtgca cccaactgat cttcagcatc ttttactttc    780
accagcgttt ctgggtgagc aaaaacagga aggcaaaatg ccgcaaaaaa gggaataagg    840
gcgacacgga aatgttgaat actcatactc ttcctttttc aatattattg aagcatttat    900
cagggttatt gtctcatgag cggatacata tttgaatgta tttagaaaaa taaacaaata    960
ggggttccgc gatgccgctc gccagtcgat tggctgagct catgaagttc ctattccgaa   1020
gttccgcgaa cgcgtaaagg atctaggtga agatcctttt tgataatctc atgaccaaaa   1080
tcccttaacg tgagttttcg ttccactgag cgtcagaccc cgtagaaaag atcaaaggat   1140
cttcttgaga tccttttttt ctgcgcgtaa tctgctgctt gcaaacaaaa aaaccaccgc   1200
taccagcggt ggtttgtttg ccggatcaag agctaccaac tctttttccg aaggtaactg   1260
gcttcagcag agcgcagata ccaaatactg tccttctagt gtagccgtag ttaggccacc   1320
acttcaagaa ctctgtagca ccgcctacat acctcgctct gctaatcctg ttaccagtgg   1380
ctgctgccag tggcgataag tcgtgtctta ccgggttgga ctcaagacga tagttaccgg   1440
ataaggcgca gcggtcgggc tgaacggggg gttcgtgcac acagcccagc ttggagcgaa   1500
cgacctacac cgaactgaga tacctacagc gtgagctatg agaaagcgcc acgcttcccg   1560
aagggagaaa ggcggacagg tatccggtaa gcggcagggt cggaacagga gagcgcacga   1620
gggagcttcc agggggaaac gcctggtatc tttatagtcc tgtcgggttt cgccacctct   1680
gacttgagcg tcgatttttg tgatgctcgt caggggggcg gagcctatgg aaaaacgcca   1740
gcaacgcggc ctttttacgg ttcctggcct tttgctggcc ttttgctcac atgttctttc   1800
ctgcgttatc ccctgattct gtggataacc gtattaccgc ctttgagtga gctgataccg   1860
ctcgccgcag ccgaacgacc gagcgcagcg agtcagtgag cgaggaagcg gaagagcgcc   1920
tgatgcggta ttttctcctt acgcatctgt gcggtatttc acaccgcata tgctggatcc   1980
ttgacagcta gctcagtcct aggtataata ctagtggcgc tgttgcgctt cctgggtttt   2040
agagctagaa atagcaagtt aaaataaggc tagtccgtta tcaacttgaa aaagtggcac   2100
cgagtcggtg cttttttga attctctaga gtcgacctgc agaactcaac taccagacca   2160
ccgctttcca cgataccgcc accgtccgtc agttgctgaa tttacggccg tcgccggagt   2220
ttgaacgctg gctggaaacg atgggcatta tggcaaacgg tcgtctgacc aaacgggcgg   2280
gcgatccgtc actgttcttc tgatgacgcg gggataacac catggatcaa aaacagattg   2340
aagaaattgt acgtagcgtg atggcgtcaa tgggacagga cgtaccgcag cccgccgcgc   2400
cgtcaacgca ggaaggcgca aagccgcagt gcgccgcgcc gacggaaatc ccttataaga   2460
attctcacac tggctcacct tcgggtgggc ctttctgcgt ttatatacta gagagagaat   2520
ataaaaagcc agattattaa tccggctttt ttattattta ggtgatccat cgaactctag   2580
aatttgacgg ctagctcagt cctaggtaca gtgctagcct agatactaga gaaagaggag   2640
aaatactaga tggttagcaa aggcgaagag ctgatcaagg agaacatgca catgaaactg   2700
tacatggaag gtaccgttaa caaccaccat tttaagtgca ccagcgaagg cgagggtaaa   2760
ccgtatgagg gcacccagac catgcgtatc aaggtggttg aaggtggccc gctgccgttt   2820
gcgttcgata ttctggcgac cagctttatg tacggcagcc gtaccttcat caaccatacc   2880
```

-continued

```
cagggtattc cggatttctt taaacagagc tttccggagg gcttcacctg ggaacgtgtg   2940

accacctacg aggacggtgg cgttctgacc gcgacccagg ataccagcct gcaagacggt   3000

tgcctgatct ataacgtgaa aattcgtggc gttaactttc cgagcaacgg tccggtgatg   3060

cagaaaaaga ccctgggctg ggaagcgaac accgagatgc tgtacccggc ggatggtggc   3120

ctggaaggtc gtagcgacat ggcgctgaag ctggttggtg gcggtcacct gatctgcaac   3180

ttcaaaacca cctatcgtag caaaaagccg gcgaaaaacc tgaagatgcc gggcgtgtac   3240

tatgttgatc atcgtctgga acgtattaaa gaggcggaca aggaaaccta cgtggaacag   3300

cacgaggtgg cggttgcgcg ttattgcgac ctgccgagca aactgggtca taagctgaac   3360

taaccaggca tcaaataaaa cgaaaggctc agtcgaaaga ctgggccttt cgttttatct   3420

gttgtttgtc ggtgaacgct ctctactaga gtcacactgg ctcaccttcg ggtgggcctt   3480

tctgcgttta taagctgggt taaccatcac tgggatcccc gtcgaggccg acagaacctg   3540

tatttcaaac attcatcagg gggggacgcc gccagtagaa gccgccgccg tgattgtgga   3600

tttggccaaa cggatgctgg agcagaaagc gtccggcatc aacatgaccc gttaaggaga   3660

catcatgcct gcattagatt taattcgacc ttcagtgact gccatgcgcg tgattgcctc   3720

cgtgaatgac ggctttgcgc gggaacttaa attaccgcca catatacgta gtctcggact   3780

catcacggca gattctgatg atgtgaccta tattgccgct gagcttagat ctattaccct   3840

gttatcccta c                                                         3851
```